United States Patent [19]
Kraus et al.

[11] Patent Number: 5,687,727
[45] Date of Patent: Nov. 18, 1997

[54] CATHETER ADAPTOR WITH SLITTING BLADE AND IMPROVED MANUAL CONTROL AND METHOD OF USE

[75] Inventors: Jeff L. Kraus, San Jose; Joseph R. Shields, Sunnyvale; Nitin P. Matani; Michael J. Horzewski, both of San Jose, all of Calif.

[73] Assignee: Danforth Biomedical Incorporated, Santa Clara, Calif.

[21] Appl. No.: 431,592

[22] Filed: May 1, 1995

[51] Int. Cl.$^6$ ............................................. A61B 6/00
[52] U.S. Cl. .............................................. 128/657; 604/161
[58] Field of Search .................................. 128/656, 657, 128/658; 604/158, 161, 164, 171, 264, 280, 284

[56] References Cited

U.S. PATENT DOCUMENTS

| | | | |
|---|---|---|---|
| 4,687,469 | 8/1987 | Osypka | 604/161 |
| 4,997,424 | 3/1991 | Little | 604/280 |
| 5,058,273 | 10/1991 | Streger | 30/164.9 |
| 5,261,887 | 11/1993 | Walker | 604/161 |
| 5,290,241 | 3/1994 | Kraus et al. | 604/161 |
| 5,322,513 | 6/1994 | Walker | 604/161 |

*Primary Examiner*—Max Hindenburg
*Attorney, Agent, or Firm*—Townsend and Townsend and Crew LLP

[57] ABSTRACT

A proximal adaptor for an over-the-wire angioplasty catheter is disclosed which contains a retractable catheter slitting element and a releasable guidewire seizing element, both of which are controllable by a manually operated element or elements accessible from the exterior of the adaptor.

18 Claims, 4 Drawing Sheets

CATHETER ADAPTOR WITH SLITTING BLADE AND IMPROVED MANUAL CONTROL AND METHOD OF USE

This invention lies in the field of catheters for percutaneous transluminal coronary angioplasty, and accessories for use with catheters of this type.

BACKGROUND OF THE INVENTION

The medical procedure known as percutaneous transluminal coronary angioplasty (PTCA) is generally performed with a guidewire-directed catheter, and catheter-guidewire assemblies which offer the greatest versatility and flexibility to the physician are those in which the catheter and guidewire can be manipulated independently. Such assemblies are commonly known as "over-the-wire" catheters, and they permit one guidewire to be exchanged for another, one catheter for another, or both, as the need arises, while leaving the unexchanged component inside the patient's vasculature to serve as a guide for positioning the component being replaced. The advantage that this offers is that it avoids requiring the physician to perform the tedious process of manoeuvering the guidewire tip more than once through the vasculature to reach the location requiring treatment.

The need for an exchange can arise for various reasons. After the initial placement of the guidewire or guidewire and catheter, the physician may for example discover that either the patient or the type of condition being treated requires a guidewire or catheter of different shape, size or other characteristic than the one already inserted. Even if the procedure is a success, however, it is desirable to leave the guidewire in place after the catheter has been removed so that the physician can monitor the patient for post-procedural spasms which might reclose the artery and require a repeat procedure. With the guidewire left in place, a new catheter can quickly be inserted.

In an over-the-wire catheter, the catheter surrounds the guidewire. As a result, the practical problem in exchanging catheters in an over-the-wire system is how to maintain a grip on the guidewire so that it can be held in place while the catheter is being pulled out. One means of accomplishing this is to use a guidewire of extraordinary length so that the portion remaining outside the patient's body exceeds the length of the catheter, thereby leaving some portion of the guidewire exposed at all times for gripping by the physician. An alternative is to attach an extension to the guidewire prior to withdrawal of the catheter, to give the guidewire the extra length needed to provide the gripping area. Either way results in an awkward procedure, with excess exposed guidewire presenting a hazard to those in the operating area and risking contact with unsterilized surfaces.

The use of excess guidewire or a guidewire extension can be avoided by using a catheter known as a "monorail" catheter, so called for its guidewire lumen which has a longitudinal opening extending the length of the tureen, permitting lateral insertion and removal of the guidewire through the opening at any location along the length of the guidewire. The catheter can thus be separated from the guidewire at locations short of the proximal end of the guidewire. A risk with this type of catheter however is its separation from the guidewire at points inside the vasculature.

A relatively new approach to the problem is the use of a device which slits the catheter from its proximal end, opening the guidewire lumen as the catheter is being withdrawn from the vasculature. This provides the advantages of a monorail catheter without the disadvantage of the risk of separation inside the vasculature. In certain constructions, this device is secured to the proximal end of the catheter for use during the angioplasty procedure as a proximal adaptor joining the catheter to other fittings and connections. The patent literature on this type of device includes Osypka, U.S. Pat. No. 4,687,469 (issued Aug. 18, 1987); Little, U.S. Pat. No. 4,997,424 (issued Mar. 5, 1991); Walker, U.S. Pat. No. 5,261,887 (issued Nov. 16, 1993); Walker, U.S. Pat. No. 5,322,513 (issued Jun. 21, 1994); and Kraus, et al., U.S. Pat. No. 5,290,241 (issued Mar. 1, 1994).

SUMMARY OF THE INVENTION

The present invention resides in a novel proximal adaptor for an over-the-wire catheter which incorporates a retractable cutting element for the catheter, manually controlled by the operator from outside the adaptor body, and in certain embodiments of the invention, a releasable clamping element for the guidewire, also controlled manually from outside the adaptor body. The invention also resides in an assembly in which the adaptor is secured to the proximal end of a catheter, ready both for use in an angioplasty procedure and for removal of the catheter from a guidewire passing through both the catheter and the adaptor. The construction of the adaptor permits the operator to engage the cutting element to slit the catheter wall and secure the guidewire against slippage, all with one hand, leaving the other hand free for handling of the catheter itself. The adaptor also permits the operator to disengage the cutting element so that it does not slit the catheter wall and to release the seizure of the guidewire, so that the adaptor can be moved longitudinally relative to the catheter and guidewire or removed completely from both.

The adaptor includes a body which contains three bores, all joined at a common juncture region. Slitting of the catheter wall occurs in the juncture region, with one bore opening to the adaptor exterior in the distal direction to receive the catheter with the guidewire inside, the second bore extending from the juncture region to receive the slit catheter after it has been separated from the guidewire, and the third bore extending from the juncture region to receive the separated guidewire. The three bores can be arranged at substantially any angle relative to each other. Preferred arrangements however are either a Y-shaped configuration in which the two branch arms serve as the second and third bores, respectively (the "Y" rotated 90° to lie on its side), or an asymmetrical Y, including for example configurations in which the first and third bores are either parallel or coaxial and the second is at an acute angle relative to the third.

Slitting of the guidewire lumen and clamping of the separated guidewire are performed by a unitary element inside the adaptor. The element is manipulated by hand from outside the adaptor, preferably using a single finger of the same hand that is holding the adaptor. In preferred embodiments of the invention, the unitary element is movable in two directions, one parallel to the adaptor body to engage the cutting element and the other transverse to the adaptor body to engage the guidewire clamp, or at an angle with components in both directions.

In further preferred embodiments of the invention, the operation of the cutting element is assisted by a guide in the juncture region which holds the catheter in place while the cutting element slits the wall adjacent to the guidewire lumen.

Other features, embodiments and advantages of the invention will be apparent from the description which follows.

DETAILED DESCRIPTION OF THE INVENTION AND PREFERRED EMBODIMENTS

Figure 1:
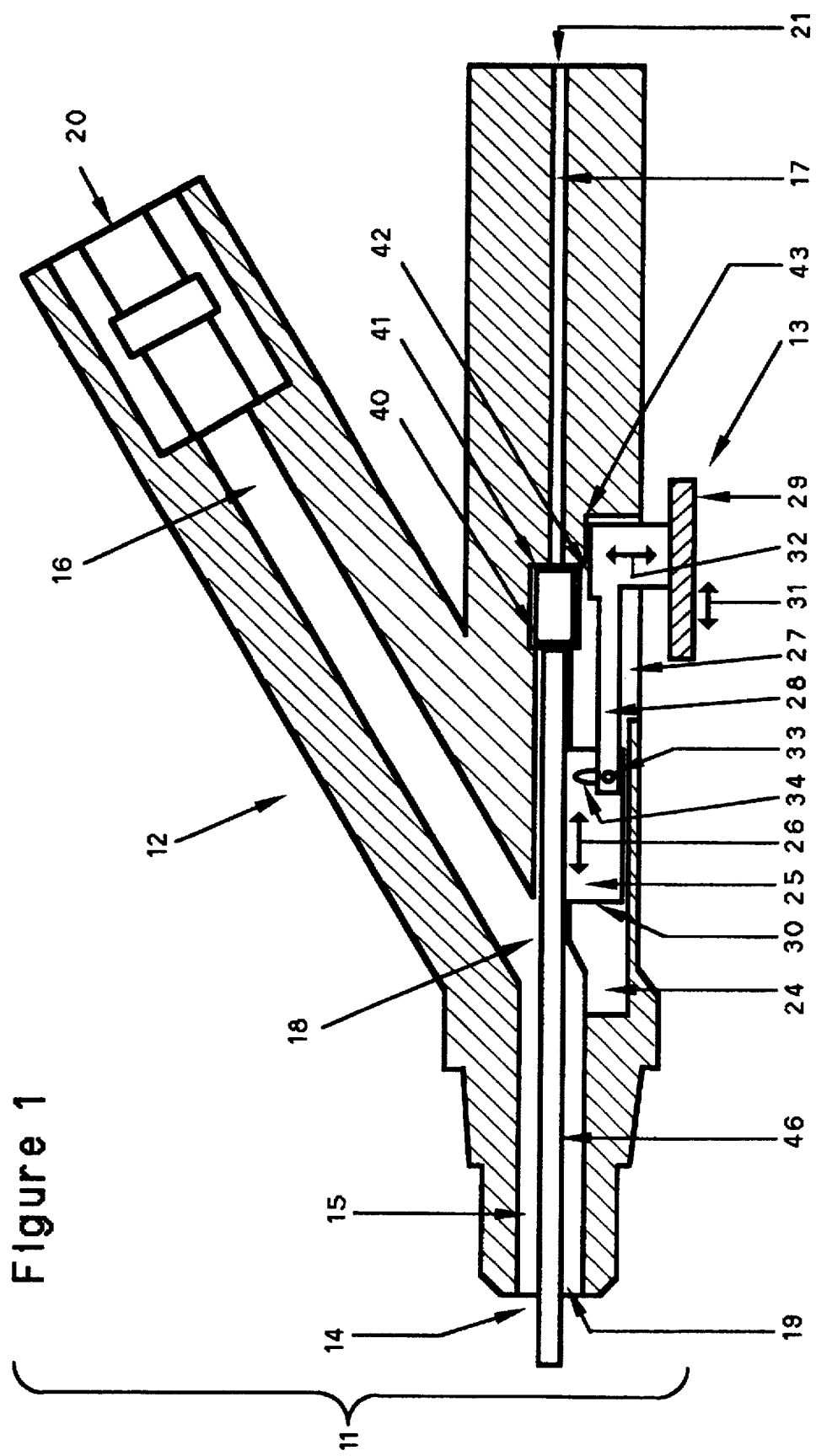
FIG. 1 is a longitudinal cross section of a proximal adaptor illustrative of the present invention, with both the cutting blade and the guidewire seizing element retracted.

While this invention can be implemented in a variety of ways and embodied in variety of structures and arrangements, the following description will focus on the device shown in the drawings, which represents one example of the invention.

The cross section view of FIG. 1 depicts the proximal adaptor 11, whose parts include a body 12 and a unitary clamping and slitting element 13 which is retained by the body but movable relative to it. The adaptor body has a distal end 14 which faces the patient's body during use. The interior of the adaptor body has three bores 15, 16 and 17, each opening to the exterior of the body at one end and joined at the other end to a juncture region 18 which is common to all three. The catheter and guidewire emerging from the patient enter the first bore 15 at the distal opening 19. The catheter is then split and separated from the guidewire in the juncture region 18, the catheter alone passing into the second bore 16 and out the proximal opening 20 of the second bore, and the guidewire alone passing into the third bore 17 and out the proximal opening 21 of the third bore. The first and second bores 15, 16 are larger in diameter than the third 17, since the third bore is the only bore through which the catheter itself does not pass. Also, in this embodiment the first and third bores are coaxial, i.e., in alignment with each other.

Included in the adaptor body 12 is a cavity 24 in which a movable cutting blade 25 is retained. The cavity 24 is sufficiently narrow (i.e., its dimension in the direction perpendicular to the plane of the drawing is sufficiently small) that the cavity limits the movement of the cutting blade to a direction parallel to the first and third bores, as indicated by the two-directional arrow 26, and prevents the blade from rotating. The cavity 24 is open both along its inner edge (i.e., the edge facing the third bore 17 and the juncture region 18) by a narrow slot (not visible in this cross section) which runs along the third bore for a portion of the length of the bore. The cavity is also open at its outer edge (the edge nearest to the exterior wall of the body 12) through a slot 27 opening to the exterior of the body.

The blade 25 is mounted on a rod 28, and a finger pad 29 extends from the rod 28 through the slot 27 and protrudes from the adaptor body 12. The finger pad 29 is movable longitudinally along the length of the slot 27 as indicated by the two-directional arrow 31 as a means of sliding the cutting blade 25 back and forth. The cutting edge 30 of the blade is its forward (distal, transverse) edge.

Included in the third bore 17 is a short length of soft, flexible tubing 40 which encircles the bore and is retained in a recess 41 in the bore wall. The recess encircles the bore and traverses the cutting blade cavity 24. The soft tubing 40 is either not bonded to the interior surfaces of the adaptor body, or is bonded only on the side opposite the cutting blade cavity 24. The side of the soft tubing which faces the cutting blade cavity can therefore be pushed inward to constrict the third bore and in so doing to clamp against the guidewire inside the bore. The tubing is readily pushed inward by the inner surface 42 of the rod 28, which itself is pushed inward and held in that position by manual pressure on the finger pad 29.

The finger pad 29 thus has two directions of motion, one which is parallel to the third bore, as indicated by the two-directional arrow 31, and the other perpendicular to the bore, as indicated by the two-directional arrow 32, or an oblique direction as a vector combination of the parallel and perpendicular directions. The finger pad is thus capable of transverse as well as longitudinal motion. The term "transverse" is used herein in the generic sense to denote any angle which has a component perpendicular to the bore. The arm 28 from which the finger pad 29 shown in the Figure extends is mounted to the cutting blade by a mounting pin 33 which provides either a pivot joint, a sliding joint, or both. For a sliding joint, the pin 33 passes through a slot 34 in the cutting blade. In an alternative arrangement, the single finger pad 29 can be replaced by two independent finger pads, one to control the longitudinal position of the cutting blade and the other to compress the soft tubing 40. The two pads can be adjacent to one another so that they can be operated with a single finger, or they can protrude from opposite sides of the adaptor body. Other geometrical arrangements will be apparent to those skilled in the art.

As an alternative to the soft tubing, seizure and immobilization of the guidewire can be achieved by the connecting arm 28 itself, pressing against the guidewire. A further alternative would be a spring-mounted or memory-biased lug affixed in the wall adjacent to the third bore for engagement by the arm or finger pad. Still further alternatives embodying the same underlying concept will be readily apparent to those skilled in the art.

When the tubing 40 is not being compressed, the rod 28 can be shifted in the proximal direction (to the right in the view shown in the Figure) so that the inner surface 42 of the rod rests on a shoulder 43 in the cavity. The shoulder allows the operator to grip the adaptor body 12 and finger pad 13 without seizing the guidewire.

Figure 2:
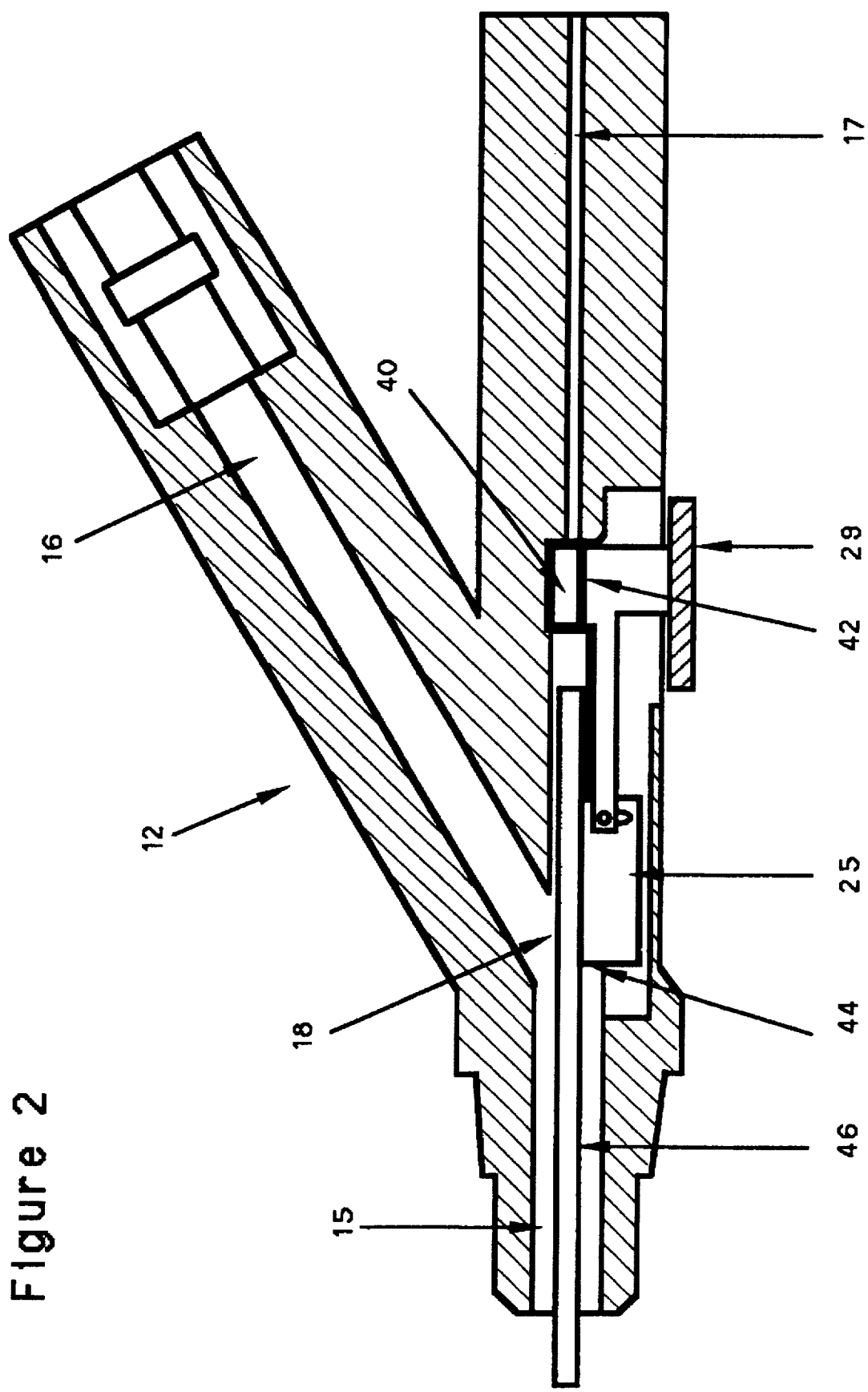
FIG. 2 is a longitudinal cross section of the proximal adaptor of FIG. 1, with both the cutting blade and the guidewire seizing element engaged.

FIG. 2 depicts the proximal adaptor with the cutting blade 25 and the clamping surface 42 in their respective engagement positions. The finger pad 29 is depressed (pushed inward relative to the adaptor body 12) and pushed forward in the distal direction (to the left in the view shown in the Figure). The inner distal corner 44 of the cutting blade is now in the juncture region 18 where the blade will pierce the catheter wall (not shown), and the soft tubing 40 is compressed into the third bore 17 where the tubing will clamp against the guidewire (not shown).

A further feature shown in FIGS. 1 and 2 is a length of rigid tubing 46 which is mounted to the cutting blade 25 along the inner longitudinal edge of the blade. This tubing is sufficiently long to extend through the juncture region 18 into the first bore 15. This tubing moves with the cutting blade and serves as a stabilizer and guide for the catheter, directing the catheter into the cutting edge 30 of the blade as the catheter is drawn back through the second bore 16. In use, the rigid tubing 46 extends into the guidewire lumen of the catheter, effectively lining the inner wall of the guidewire lumen and surrounding the guidewire, which passes through the tubing into the third bore 17. The portion of the catheter wall residing inside the juncture region 18 of the adaptor body is pre-slit to permit the catheter to separate from the rigid tubing 46 at that point and pass into the second bore 16.

Figure 3:
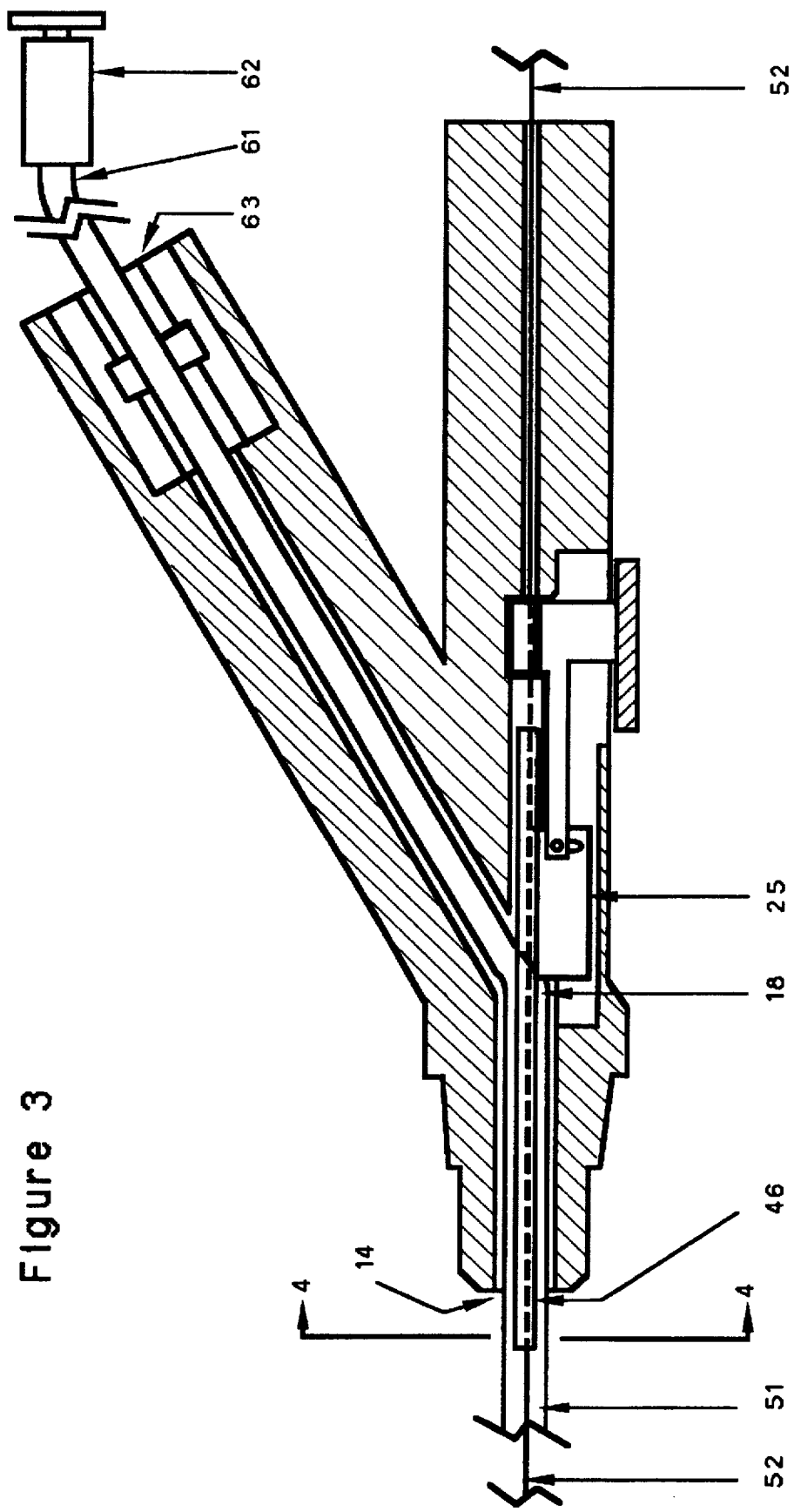
FIG. 3 is a longitudinal cross section identical to that of FIG. 2, with a catheter and guidewire included.
Figure 4:
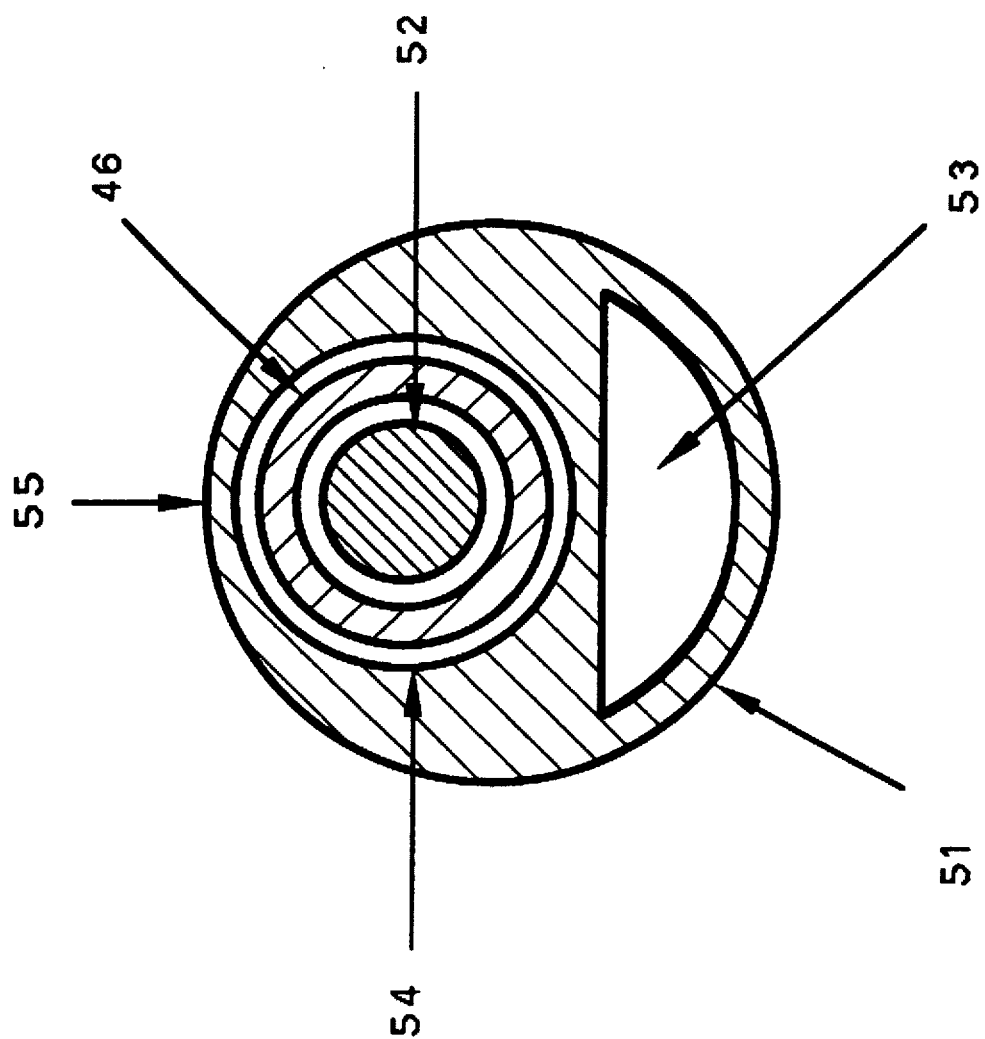
FIG. 4 is a transverse cross section taken along the line 4—4 of FIG. 3.

FIG. 3 illustrates the proximal adaptor with a catheter and guidewire passing through it, and FIG. 4 is a transverse cross section taken along the line 4—4 of FIG. 3. Entering the adaptor from the distal end 14 are the combined catheter body 51 and guidewire 52. FIG. 4 shows that the catheter body contains two adjacent lumens, the inflation lumen 53 and the guidewire lumen 54. The rigid tubing 46 passes through the guidewire lumen 54, and the guidewire 52 passes through the rigid tubing 46. In the juncture region 18 of the adaptor body, the cutting blade 25 pierces the outer wall of the guidewire lumen at the location 55 indicated in FIG. 4, opening the tureen to permit the catheter body 51 to be pulled away from the tubing 46 and hence the guidewire 52.

The proximal end 61 of the catheter is fed by a source of inflation fluid 62 and appropriate pressurizing equipment and other units of the conventional type used with angioplasty equipment (not shown). These units and the inflation fluid source are sealed to the inflation lumen 53 in fluid-fight manner. The catheter can be secured to the proximal adaptor body by a conventional fitting such as a LUER-LOK fitting, one part of which 63 is shown, or by use of a retaining clip (not shown).

Once the catheter has been slit and removed, either a monorail catheter as described above or a new over-the-wire catheter with a guidewire extension can be used as a replacement.

The foregoing is offered primarily for purposes of illustration. It will be readily apparent to those skilled in the art that the materials, dimensions, component shapes and configurations and other parameters of the device described herein may be further modified or substituted in various ways without departing from the spirit and scope of the invention.

What is claimed is:

1. A proximal adaptor for securement to a proximal end of a catheter containing a lumen to receive a guidewire and to permit longitudinal movement of said catheter relative to said guidewire, said proximal adaptor comprising:
   a body containing first, second and third bores, joined at a common juncture region, said first and second bores each being of sufficient cross section to receive said catheter, and said third bore being of sufficient cross section to receive said guidewire;
   a cutting member slidably retained inside said body for movement between a cutting position and a retracted position; and
   cutting member manipulating means for manually manipulating said cutting member from outside said body.

2. A proximal adaptor in accordance with claim 1 in which a cutting edge of said cutting member resides in said juncture region when said cutting member is in said cutting position, and said cutting edge is displaced from said juncture region when said cutting member is in said retracted position.

3. A proximal adaptor in accordance with claim 1 further comprising a guide in said first bore arranged to stabilize a catheter within said body and maintain alignment of said catheter with said cutting member.

4. A proximal adaptor in accordance with claim 3 in which said guide is a rigid tubular member mounted to said cutting member.

5. A proximal adaptor in accordance with claim 1 in which said first and third bores are in alignment with one another along a common axis, and said cutting member is slidably retained inside said body for movement along said axis.

6. A proximal adaptor in accordance with claim 1 further comprising a releasable seizing member mounted in said body to constrict said third bore, and compressing means for compressing said releasable seizing member into a constricting position.

7. A proximal adaptor in accordance with claim 6 in which said releasable seizing member is length of flexible tubing mounted inside said third bore.

8. A proximal adaptor in accordance with claim 6 in which said cutting member manipulating means and said compressing means are combined into a single means comprising a support member joined to said cutting member, accessible from outside said body, and movable to compress said releasable seizing member into said constricted position.

9. A proximal adaptor in accordance with claim 8 in which said single means further comprises a protuberance extending from said support member through an opening in a side wall of said body to the exterior of said body.

10. A proximal adaptor in accordance with claim 9 in which said opening is a slot permitting sliding movement of said protuberance parallel to said side wall of said body.

11. A proximal adaptor in accordance with claim 9 in which said opening is a slot permitting sliding movement of said protuberance parallel to said side wall of said body, and said protuberance is movably joined to said cutting member to permit movement of said protuberance in a direction transverse to said side wall.

12. A catheter and proximal adaptor assembly, comprising:
   a catheter containing first and second lumens, defined as an inflation lumen and a guidewire lumen, respectively, said guidewire lumen adjacent to an external catheter wall;
   a holding member encircling said catheter and containing first, second and third bores joined at a common juncture region, said catheter extending through said first bore, said juncture region and said second bore;
   a cutting member slidably retained inside said holding member for movement between (i) a cutting position in which said cutting member is in contact with said catheter, piercing through said external catheter wall to said guidewire lumen and (ii) a retracted position in which said cutting edge is out of contact with said catheter; and
   cutting member manipulating means for manually manipulating said cutting member from outside said body.

13. A catheter and proximal adaptor assembly in accordance with claim 12 further comprising a rigid tubular member mounted to said cutting member and extending through said external catheter wall into said guidewire lumen.

14. A catheter and proximal adaptor assembly in accordance with claim 12 further comprising a releasable seizing member mounted in said body to constrict said third bore, and compressing means for compressing said releasable seizing member into a constricting position while holding said cutting member in said cutting position.

15. A catheter and proximal adaptor assembly in accordance with claim 14 in which said releasable seizing member is a length of flexible tubing mounted inside said third bore.

16. A catheter and proximal adaptor assembly in accordance with claim 14 in which said cutting member manipulating means and said compressing means are combined into a single means comprising a support member joined to said cutting member and accessible from outside said holding member, said support member being movable to compress said releasable seizing member into said constricted position.

17. A catheter and proximal adaptor assembly in accordance with claim 12 further comprising means for supplying pressurized fluid to said inflation lumen independently of said guidewire lumen.

18. A method for removing a catheter from a patient while leaving a guidewire in position, said guidewire passing through a lumen in said catheter and having served to facilitate the positioning of said catheter in said patient, said catheter and said guidewire both having proximal and distal ends, said method comprising:

(a) securing said proximal ends of said catheter and said guidewire in a proximal adaptor comprising:
 (i) a body containing first, second and third bores, joined at a common juncture region, with said catheter passing through said first bore, said juncture region, and said second bore, and said guidewire passing through said first bore, said juncture region and said third bore, said catheter being pre-slit at said juncture region to permit separation of said guidewire from said catheter;
 (ii) a cutting member slidably retained inside said body for movement between a cutting position in said juncture region and a retracted position; and
 (iii) cutting member manipulating means for manually manipulating said cutting member from outside said body;

(b) manually holding said cutting member manipulating means in said cutting position to engage said catheter, and drawing said catheter proximally through said first and second bores across said cutting member, thereby separating said catheter from said guidewire at said juncture region while retaining said guidewire substantially stationary relative to said proximal adaptor.

* * * * *